United States Patent

Mantell et al.

Patent Number: 5,292,304
Date of Patent: Mar. 8, 1994

[54] INSUFFLATOR DIGITAL GAS FLOW SYSTEM

[75] Inventors: Robert R. Mantell, Arlington Heights; Albert Nowesielski, Roselle; Charles Zander, Grayslake, all of Ill.

[73] Assignee: Northgate Technologies, Inc., Arlington Heights, Ill.

[21] Appl. No.: 892,049

[22] Filed: Jun. 2, 1992

[51] Int. Cl.⁵ .............................. A61M 37/00
[52] U.S. Cl. .............................. 604/26; 604/23
[58] Field of Search ............... 604/23, 26, 30, 24, 604/25; 128/747, 204.21

[56] References Cited

U.S. PATENT DOCUMENTS

| | | | |
|---|---|---|---|
| 4,676,774 | 6/1987 | Semm et al. | 604/26 |
| 4,966,578 | 10/1990 | Baier et al. | 604/26 |
| 5,013,294 | 5/1991 | Baier | 604/26 |
| 5,098,375 | 3/1992 | Baier | 604/26 |
| 5,139,478 | 8/1992 | Konincky et al. | 604/26 |
| 5,152,745 | 10/1992 | Steiner et al. | 128/747 |
| 5,199,944 | 4/1993 | Cosmisun | 604/26 |

Primary Examiner—C. Fred Rosenbaum
Assistant Examiner—Manuel Mendez
Attorney, Agent, or Firm—Robert M. Wolters

[57] ABSTRACT

A pressure controlling system for an insufflator includes a plurality of parallel connected, solenoid controlled valves. Each valve has in series therewith a gas flow limiter with the limiters arranged in digital succession. The valves are in parallel with one another and in series with the gas flow line so that solenoid opening of one or more of the valves controls gas flow in an on-off fashion with gas flow continuing through the respective flow limiting means to determine total flow rate in a digital manner.

10 Claims, 1 Drawing Sheet

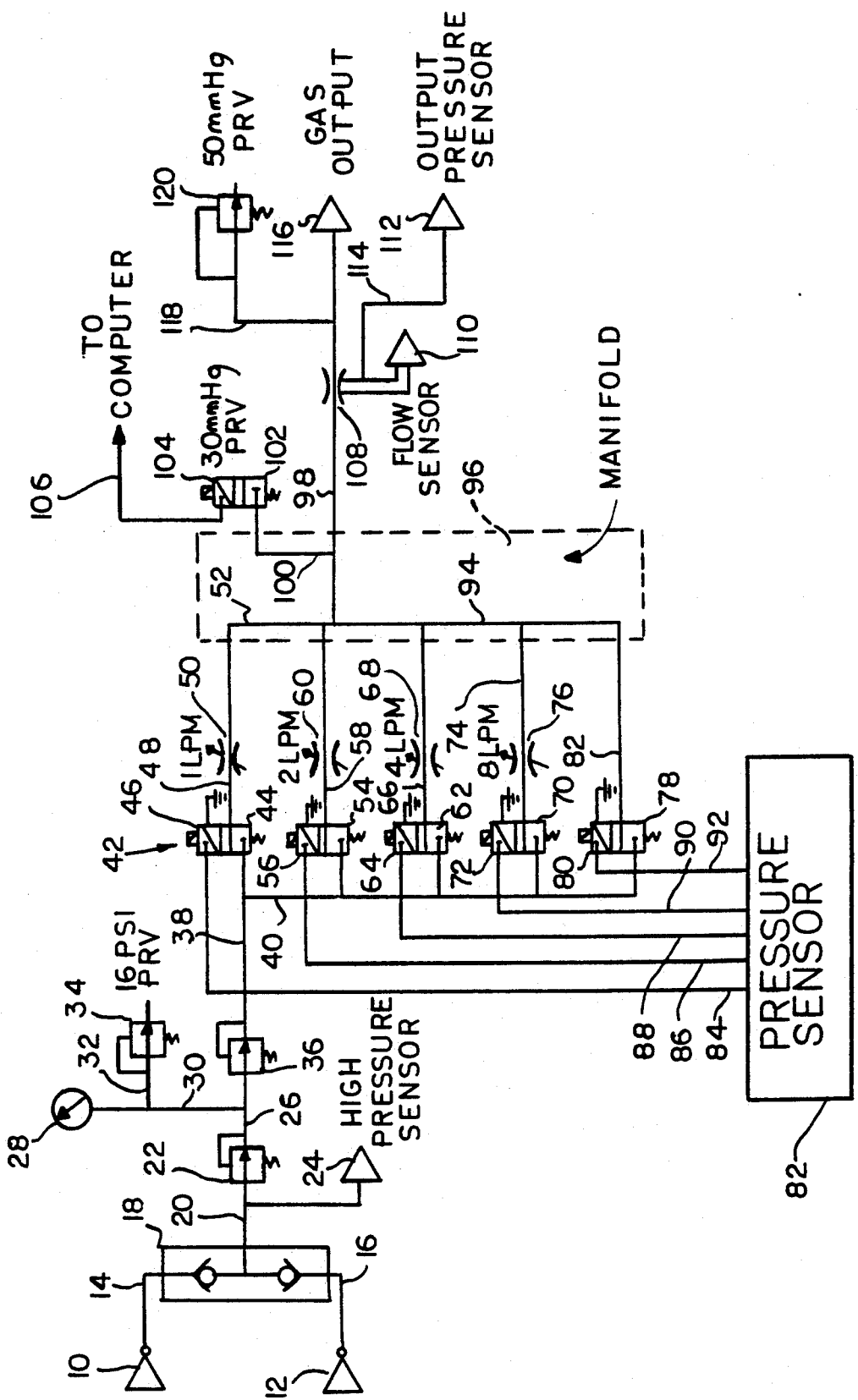

INSUFFLATOR DIGITAL GAS FLOW SYSTEM

BACKGROUND OF THE INVENTION

Laparoscopic surgery, performed through very small incisions in the patient, has markedly lessened patient trauma and hospitalization time. In performing laparoscopic surgery it is often desirable to apply internal gas pressure, usually carbon dioxide or argon gas to expand the working space. Such gas expansion procedure is referred to as insufflation, and the pressure within the insufflated space must be controlled quite precisely. The instruments for introducing and releasing gas are known as trochars, and are essentially hollow spikes which are stabbed through the patient's epidermis and into the working area. Too much pressure can cause obvious damage, while too little pressure can allow the pointed tips of the trochars to engage internal organs with consequent damage.

Commercial insufflators generally have some means for measuring internal pressure, and often for automatic regulation of pressure. However, such pressure has generally been controlled by analog devices which inprecise in nature.

OBJECTS AND SHORT SUMMARY OF THE INVENTION

In accordance with the present invention it is an object thereof to provide control of pressure within the insufflated space utilizing digital binary progression flow control.

More particularly, it is an object of this invention to provide a plurality of solenoid controlled gas valves which are either fully opened or fully closed to provide digital control of gas flow into the insufflated volume.

In carrying out the principles of the present invention we supply a plurality of parallel valves respectively in series with flow limiters of respective different capacity. A first valve and limiter combination is capable of passing 1 liter per minute, a second 2 liters per minute, a third 4 liters per minute, and a fourth 8 liters per minute. Pressure within the insufflated space is measured, and one or more of the valves is opened in parallel to supply sufficient volume of gas inflow to attain and maintain the desired pressure within the insufflated space.

THE DRAWING

The invention will best be understood with reference to the attached drawing and the following specification. The drawing consists of a single figure as follows:

FIG. 1 is a schematic electrical and flow diagram of the present invention.

DETAILED DESCRIPTION OF THE ILLUSTRATED EMBODIMENT

Two gas input connections are provided at 10 and 12, and are conventional in nature, generally comprising threaded fittings on gas conducting lines 14 and 16 for screwing on to gas bottles. Both bottles should be of the same type, usually carbon dioxide, although argon is sometimes used. The gas supply lines 14 and 16 are connected to an input selector 18. The input selector has a shuttle valve member that slides back and forth in accordance with the pressure in the two bottles connected to the inputs 10 and 12, whereby the gas supplied at higher pressure (bottle having greater gas content) is connected to an output line 20 from the input selector.

A high pressure regulator 22 is connected in the output line 20, and a high pressure sensor 24 is also connected to this line to provide a readout of the supply pressure.

The gas conveying line continues at 26 from the high pressure regulator, and a pressure gauge 28 is connected thereto for a readout of the lowered pressure. The line 30 connecting the gas conveying line 26 and the pressure gauge 28 has a lateral connection at 32 leading to a pressure release valve 34. Typically the pressure release valve 34 is set for 16 pounds per square inch, whereby if the pressure in the gas conveying line 26 is higher than 16 pounds per square inch the pressure relief valve will open, and simply blow off the carbon dioxide or other gas into the air.

The gas conveying line continues to a low pressure regulator 36 having an output gas flow line 38 with a parallel branch 40 leading to a parallel bank of solenoid controlled valves 42. The first of these valves 44 is controlled, either on or off, by a solenoid 46, and has an output line 48 leading to a restrictive device 50 which will convey 1 liter per minute of gas to a collector line 52.

A second valve 54, also either on or off, is controlled by a solenoid 56 and has an output flow line 58 connected through a flow restrictive device 60 restricted to 2 liters per minute and leading to the collector line 52.

The third solenoid controlled valve 62 is controlled by a solenoid 64 to be either on or off, and has a output line 66 leading to a flow restricting device 68 limiting flow to 4 liters per minute, and connected to the collector line 52.

A fourth parallel solenoid valve 70 controlled by a solenoid 72 to be either on or off is connected to a flow line 74 leading to a restrictive device 76 limited to 8 liters per minute.

An optional fourth valve 78 is connected to the line 40 and is controlled by a solenoid 80 to be either on or off. The optional valve 78 leads through a line 82 directly to the collector line 52 without a limiter. Obviously, a limiter can be provided if desired. The limiters are of conventional nature, and simply may comprise an orifice that will allow gas to flow only at a certain maximum rate. The fifth valve 78 is optionally provided to allow greater flow rates should they be needed. In some instances, it may be difficult to obtain a valve 70 that will provide a full 8 liters per minute flow, and in this case additional flow may be provided by the valve 78. Pressure sensor apparatus 82 measures the pressure of the insufflator volume within the patient. An electric line 84 or other conductor extends from the pressure sensor to the first valve solenoid 46. A second conductor 86 leads from the pressure sensor 82 to the second solenoid 56. A third conductor 88 leads from the pressure sensor to the third solenoid 64, a fourth conducter 90 leads from the pressure sensor to the solenoid 72, and a further conducter 92 leads from the pressure sensor to the fifth solenoid 80 when the valve 78 is provided. If pressure in the insufflated space is just a little bit low the sensor will energize the line 84 to open the solenoid controlled valve 44 through actuation of the solenoid 46. Gas is passed through the limiter 50 at 1 liter per minute to insufflate the volume, or to maintain it insufflated. Obviously, a larger volume will be required at the start to fill up the space than is required to maintain equilibrium within the space or volume. Similarly, the valves 54, 62 and 70 (and the valve 78 when provided) are selectively opened to provide a digital control of flow. Obviously, opening of the first valve 44 allows 1 liter per minute to flow. Opening only of the second valve 54 allows 2 liters per minute to flow, while opening of both valves 44 and 54 allows 3 liters per minute to flow. Opening of the valve 62 with the valves 44 and 54 closed allows 4 liters per minute to flow, while the valve 44 may be opened in addition to the valve 62 to allow 5 liters per minute to flow, while opening of valve 54 in addition to valve 62 allows 6 liters per minute to flow, and opening of all three valves 44, 54 and 62 allows 7 liters per minute to flow. Similarly, sole opening the valve 70 allows 8 liters per minute to flow, while opening of this valve with selective opening the valves 44, 54 and 62 will allow up to 15 liters per minute to flow. Further opening of the valve 78 when provided may allow additional gas flow, as desired. All of the gas flow goes to an output gas flow line 92 in a manifold 96, and this line 94 leads to an output line 98 having a lateral connection at 100 to a valve 102 controlled by a solenoid 104 which is connected to a computer at 106 for control by software in the computer. The valve 102 is a pressure relief valve, and this valve may be operated from time to time as necessary under control of computer software to maintain a maximum pressure in the line 98 at 30 millimeters of mercury.

The line 98 continues through a flow sensor 108 which has a connection 110 to provide a readout of the volume of flow. An output pressure sensor connection is provided at 112 through a line 114 to the flow sensor, whereby to provide a readout of output pressure.

The line 98 continues after the flow sensor 108 to a gas outlet 116 which is connected to the input trochar to the patient. A lateral gas flow line at 118 leads from the line 98 to a pressure relief valve 120 set at 50 millimeters of mercury to provide absolute control against severe overpressure.

It will now be apparent that the pressure sensor provides individual control for the parallel bank of valves 42 to provide a precise digital control of gas flow, thus improving over the previous somewhat unreliable analog controls known. Furthermore, it is not necessary to use valves 44, 54, 62, 70 and 78 of different sizes, which can present some confusion in assembly operations. The valves and their associated solenoids all can be the same, since it is only important that they be open or closed. The flow rate of each valve is controlled by the associated flow limiter 50, 60, 68, and 76.

The specific example of the invention as herein shown and described is for illustrative purposes only. Various changes in structure will no doubt occur to those skilled in the art, and will be understood as forming a part of the present invention insofar as they fall within the spirit and scope of the appended claims.

The invention is claimed as follows:

1. A digital flow controlling system for an insufflator comprising means for connection to a source of pressurized insufflating gas, input flow means connected to said connection means in gas flow relation therewith, a plurality of gas flow control means of differing flow capacities in digital capacity relation to one another, the first of said plurality of gas flow control means having a fixed rate of flow of one unit of gas, and each succeeding one of said gas flow control means having a fixed rate of flow which is twice the unit flow rate of the preceding gas flow control means, each having an input end and an output end and each including an on-off valve, means connecting the input ends of said plurality of said gas flow control means in continuously open gas flow relation in parallel with one another
to said input flow means, output gas flow means, means connecting the output ends of said gas flow control means in continuously open gas flow relation in parallel with one another to said output gas flow means, and means for selectively opening and closing said on-off valves singly and in combination to provide digitally differing rates of gas flow to said output gas flow means.

2. A system as set forth in claim 1 wherein said plurality of said gas flow control control means equals at least 4 gas flow control means, respectively having fixed flow rates of one unit of gas, two units of gas, four units of gas, and eight units of gas.

3. A system as set forth in claim 1 wherein at least some of said gas flow control means have flow limiting means in series with said valves.

4. A system as set forth in claim 2 wherein at least some of said gas flow control means have flow limiting means in series with said valves.

5. A system as set forth in claim 3 wherein all of said valves are the same and gas flow volume is controlled by said flow limiting means.

6. A system as set forth in claim 1 wherein each of said valves comprises a solenoid controlled valve.

7. A system as set forth in claim 6 wherein each of said valves is the same, and further including a plurality of flow limiting means respectively in series with said valves.

8. A system as set forth in claim 1 wherein the means for selectively opening and closing said valves comprises pressure sensing means adapted to measure the pressure in a patient being insufflated.

9. A system as set forth in claim 1 wherein said connecting means comprises a pair of connectors respectively adapted to be connected to one of two bottles of insufflating gas, and further including pressure sensitive interconnecting means between said connectors and said input gas flow means selectively to connect said connectors with said input gas flow means in accordance with gas pressure in bottles connected to said connectors.

10. A system as set forth in claim 9 wherein the means sensitive to the pressures in gas bottles connected to said conductors comprises a shuttle valve.

* * * * *